(12) United States Patent
Song et al.

(10) Patent No.: US 11,357,812 B2
(45) Date of Patent: Jun. 14, 2022

(54) **COMPOSITION CONTAINING *DOLICHOS LABLAB* LINN. EXTRACT AS ACTIVE INGREDIENT FOR EASING HANGOVERS, AND PREVENTING, ALLEVIATING OR TREATING ALCOHOLIC GASTROINTESTINAL DISEASES**

(71) Applicant: KOREA INSTITUTE OF ORIENTAL MEDICINE, Daejeon (KR)

(72) Inventors: Kwang-Hoon Song, Daejeon (KR); Yun Hee Kim, Gwacheon-si (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 140 days.

(21) Appl. No.: 16/470,453

(22) PCT Filed: Dec. 14, 2017

(86) PCT No.: PCT/KR2017/014679
§ 371 (c)(1),
(2) Date: Jun. 17, 2019

(87) PCT Pub. No.: WO2018/110988
PCT Pub. Date: Jun. 21, 2018

(65) Prior Publication Data
US 2019/0314437 A1    Oct. 17, 2019

(30) Foreign Application Priority Data

Dec. 16, 2016 (KR) .................. 10-2016-0172804

(51) Int. Cl.
*A61K 36/00* (2006.01)
*A61K 36/48* (2006.01)
*A61P 25/32* (2006.01)

(52) U.S. Cl.
CPC .............. *A61K 36/48* (2013.01); *A61P 25/32* (2018.01)

(58) Field of Classification Search
CPC .......... A23V 2200/32; A23V 2200/334; A61P 25/32; A23L 33/10
See application file for complete search history.

(56) References Cited

FOREIGN PATENT DOCUMENTS

| CN | 101878835 A | * | 11/2010 |
| CN | 102091282 A | * | 6/2011 |
| CN | 103520607 B | * | 5/2014 |
| JP | 2013-203683 A | | 10/2013 |
| KR | 100316296 B1 | | 12/2001 |
| KR | 1020030007987 A | | 1/2003 |
| KR | 100552398 B1 | | 2/2006 |
| KR | 1020140116283 A | | 10/2014 |
| KR | 1020160065497 A | | 6/2016 |
| KR | 101661145 B1 | | 9/2016 |
| WO | 2016/060426 A1 | | 4/2016 |

OTHER PUBLICATIONS

Tarin et al, Gastroprotective Effects of Bauhinia purpurea, Dolichos lablab and Vitex parviflora. Latin American Journal of Pharmacy , (Apr. 2011) vol. 30, No. 3, pp. 558-562 (Year: 2011).*
"Hyperhidrosis and Herb—Dolichos Lablab Linne", Naver blog [online], Nov. 27, 2015, 4 pages, Internet <URL: https://blog.naver.com/cjle0105/220543782643>.
"Dolichos Lablab Linne = Lablab Bean = Hyacinth Bean", Daum blog [online], Jul. 29, 2011, 7 pages, Internet <URL: http://blog.daum.net/dirchmdwjs/6796460>, English abstract.
International Searh Report for PCT/KR2017/014679 dated Mar. 20, 2018.
Dolichoris Semen, Retrieved from the Internet <https://web.archive.orglweb/20040908213311/http://www.ikkando.com/minkan/syoyaku/hakuhenzu.pdf>, Published online Sep. 8, 2004.
Japanese Notice of Allowance for Application No. 2019-554458 dated Jun. 1, 2021.

* cited by examiner

*Primary Examiner* — Qiuwen Mi
(74) *Attorney, Agent, or Firm* — Cantor Colburn LLP (57) ABSTRACT

The present invention relates to a composition containing *Dolichos lablab* Linn. extract as an active ingredient for easing hangovers, and preventing, alleviating or treating alcoholic gastrointestinal diseases, the composition having an effect in restoring gastrointestinal wall damaged by alcohol consumption, and being capable of reducing alcohol and acetaldehyde content in the blood as well as increasing aldehyde dehydrogenase activity therein. Therefore, the *Dolichos lablab* Linn. extract according to the present invention can be used for easing hangovers, and as healthy functional food or medicine that can prevent, alleviate or treat alcoholic gastrointestinal diseases.

8 Claims, 6 Drawing Sheets

EtOH + Dolichos lablab Linn. extract (400 mg/kg)

COMPOSITION CONTAINING *DOLICHOS LABLAB* LINN. EXTRACT AS ACTIVE INGREDIENT FOR EASING HANGOVERS, AND PREVENTING, ALLEVIATING OR TREATING ALCOHOLIC GASTROINTESTINAL DISEASES

TECHNICAL FIELD

The present invention relates to a composition containing *Dolichos lablab* Linn. extract as an active ingredient for easing hangovers, and preventing, alleviating or treating alcoholic gastrointestinal diseases.

BACKGROUND ART

If you drink alcohol until you are drunk, you may experience the toxicity of alcohol and its intermediate metabolite, acetaldehyde, dehydration, nutrient deficiencies (blood sugar, mineral, and vitamin deficiencies) due to malabsorption, etc. The symptoms greatly vary depending on the individual differences (genetic inheritance), environmental conditions (nutritional status, exercise status, degree of dehydration, health status, etc.).

Alcohol is oxidized to acetaldehyde in the liver by alcohol dehydrogenase (ADH) and the coenzyme $NAD^+$, and acetaldehyde is degraded into acetic acid by aldehyde dehydrogenase (ALDH) and $NAD^+$. Alcohol is also oxidized to acetaldehyde by cytochrome P-450 type 2E1 (CYP2E1) and catalase. It is known that acetaldehyde and acetic acid cause lipid peroxidation, etc., which lead to cytotoxicity, headache or abdominal pain, dehydration resulting from osmotic pressure changes, etc. In addition, excessive alcohol consumption may cause gastrointestinal diseases, and in severe cases, it may cause gastritis or gastric ulcer. Frequent consumption of alcohol in addition to social stress is often accompanied by severe gastric ulcer and liver diseases. Thus, many medicines and healthy functional foods are on the market to alleviate them. Research efforts have been mainly focused on activating ADH and ALDH and thereby lowering the blood alcohol concentration. However, there are few studies on the promotion of degradation of the alcohol ingested due to alcohol consumption or the alleviation of the resultant gastrointestinal diseases.

*Dolichos lablab* Linn., which is also called lablab bean, Egyptian bean or kidney bean, has alternate, compound, trifoliate leaves. The stipules are small and triangular, and the leaflets are broadly ovate and acute. The leaves on the stems have a wide wedge or block shape with flat edges and are thinly hairy on both sides. The flowers are butterfly-shaped and white. The seeds are white and there are 2 to 5 seeds in each pod.

Korean Patent No. 0316269 discloses the effect of the methanol extract of lablab bean leaves in increasing physiological activity. Korean Patent No. 1661145 discloses a composition containing *Dolichos lablab* Linn. extract as an active ingredient for preventing or alleviating nonalcoholic fatty liver diseases. Korean Patent Laid-Open No. 2016-0065497 discloses a method for the preparation of beverages for easing hangovers and a beverage for easing hangovers. However, a composition containing *Dolichos lablab* Linn. extract as an active ingredient for easing hangovers, and preventing, alleviating or treating alcoholic gastrointestinal diseases has not been reported yet.

SUMMARY OF INVENTION

Technical Problem

The present invention has been made in view of the above needs. The present invention provides a composition containing *Dolichos lablab* Linn. extract as an active ingredient for easing hangovers, and preventing, alleviating or treating alcoholic gastrointestinal diseases. The present inventors have found that the *Dolichos lablab* Linn. extract as an active ingredient has the effect of reducing alcohol and acetaldehyde content in the blood and increasing aldehyde dehydrogenase activity, and particularly of protecting the gastrointestinal wall damaged by alcohol consumption, and thereby completed the present invention.

Solution to Problem

In order to achieve the object, the present invention provides a healthy functional food composition containing *Dolichos lablab* Linn. extract as an active ingredient for easing hangovers, and preventing or alleviating alcoholic gastrointestinal diseases.

Also, the present invention provides a pharmaceutical composition containing *Dolichos lablab* Linn. extract as an active ingredient for easing hangovers, and preventing or treating alcoholic gastrointestinal diseases.

Advantageous Effects of Invention

The present invention relates to a composition containing *Dolichos lablab* Linn. extract as an active ingredient for easing hangovers, and preventing, alleviating or treating alcoholic gastrointestinal diseases. The composition has the effect of alleviating or treating the stomach damaged by alcohol consumption, and thus can be used for healthy functional foods or medicines for patients suffering from alcoholic gastritis or gastric ulcer.

BRIEF DESCRIPTION OF DRAWINGS

FIGS. 2A and 2B show the results of measurement of the acetaldehyde content and the aldehyde dehydrogenase activity in the blood over time (0, 30, 60, 120 and 180 minutes) after administration of ethanol and administration of the *Dolichos lablab* Linn. extract of the present invention. FIG. 2B shows the content of acetaldehyde. "Control" represents a normal group not subjected to any treatment. "EtOH+vehicle" represents a group administered with ethanol. "EtOH+*Dolichos lablab* Linn. extract (400 mg/kg)" represents a group administered with ethanol and *Dolichos*

*lablab* Linn. extract. "#" and "##" indicate that the blood acetaldehyde content of the ethanol-administered group statistically significantly increased or the aldehyde dehydrogenase activity thereof statistically significantly decreased compared to the normal group, "#" indicating $p<0.05$ and "##" indicating $p<0.01$. "*" indicates that the blood acetaldehyde content of the group administered with ethanol and *Dolichos lablab* Linn. extract statistically significantly decreased or the aldehyde dehydrogenase activity thereof statistically significantly increased with $p<0.05$ compared to the ethanol-administered group.

FIGS. 3A to 3F show the results of H&E staining of stomach and liver tissues to determine the effect of a hot water extract of *Dolichos lablab* Linn. on the stomach and liver damage caused by alcohol.

DESCRIPTION OF EMBODIMENTS

Embodiments

The present invention relates to a healthy functional food composition containing *Dolichos lablab* Linn. extract as an active ingredient for easing hangovers, and preventing or alleviating alcoholic gastrointestinal diseases.

As used herein, the hangover is a phenomenon caused by accumulation of alcohol or acetaldehyde in the body due to lack of alcohol dehydrogenase (ADH), which degrades alcohol, or aldehyde dehydrogenase (ALDH), which degrades acetaldehyde, in a drunken state. Representative symptoms of hangover include nausea, dizziness, vomiting, thirst, lethargy, headache, myalgia, indigestion, abdominal pain, and diarrhea.

The alcoholic gastrointestinal diseases are preferably nausea, vomiting, abdominal pain, indigestion, alcoholic gastritis or alcoholic gastric ulcer, although not limited thereto.

The *Dolichos lablab* Linn. extract can promote the degradation of alcohol and acetaldehyde in the blood and increase aldehyde dehydrogenase activity.

Conventional extraction solvents known in the art may be used for the *Dolichos lablab* Linn. extract. Preferred extraction solvents are water, $C_1$-$C_4$ anhydrous or hydrated lower alcohols (e.g., methanol, ethanol, propanol, butanol, n-propanol, isopropanol and n-butanol), a mixed solvent of the lower alcohol and water, acetone, ethyl acetate, chloroform, 1,3-butylene glycol, hexane, diethyl ether, or butyl acetate, more preferably water, ethanol or a mixed solvent thereof, still more preferably water. In the case of hot water extraction using water, water was added in an amount 5 to 10 times by volume relative to the weight of *Dolichos lablab* Linn. and heated at 90 to 110° C. for 2 to 3 hours to perform extraction. Preferably, the extracted solution is filtered through a filter paper and then lyophilized for use, although not limited thereto. In the case of ethanol extraction, 80% ethanol was added in an amount 5 to 10 times by volume relative to the weight of *Dolichos lablab* Linn, and the *Dolichos lablab* Linn was immersed at a room temperature of 20 to 25° C. for 22 to 24 hours to perform extraction. Preferably, the extracted solution is filtered through a filter paper and then lyophilized for use, although not limited thereto.

The healthy functional food composition of the present invention may be prepared into a formulation selected from powders, granules, pills, tablets, capsules, candies, syrups and beverages, although not limited thereto. The extract includes any one of a liquid extract obtained by extraction treatment, a diluted or concentrated liquid of the liquid extract, a dry product prepared by drying the liquid extract, or a crude purified product or a purified product thereof. The healthy functional food composition is not particularly limited as long as it can be ingested to ease hangovers and prevent or alleviate alcoholic gastrointestinal diseases. When the healthy functional food composition of the present invention is used as a food additive, the composition may be added as it is or in combination with other foods or food ingredients, and may be appropriately used according to a conventional method. The amount of the active ingredient may be appropriately determined according to the intended use (for prevention or alleviation). In the preparation of foods or beverages, the active ingredient is generally added in an amount of 15 parts by weight or less, preferably 10 parts by weight or less, relative to the healthy functional food composition of the present invention. However, in the case of long-term intake for health control purposes, the amount may be less than the above range. Also, the active ingredient may be used in an amount exceeding the above range since it has no problem with safety. The types of the foods are not particularly limited. Examples of the foods to which the healthy functional food composition can be added include meats, sausages, bread, chocolate, candies, snacks, confectionery, pizzas, ramen, other noodles, gums, dairy products including ice creams, various soups, beverages, teas, drinks, alcoholic beverages and multi-vitamin preparations. The foods include all health foods in a conventional sense. The healthy functional food composition of the present invention may also be prepared into a food, particularly a functional food. The functional food of the present invention contains ingredients conventionally added in the preparation of foods, for example, proteins, carbohydrates, fats, nutrients and seasonings. For example, when it is prepared into a drink, it may contain a natural carbohydrate or a flavoring agent in addition to the active ingredient. Preferably, the natural carbohydrate is a monosaccharide (e.g., glucose and fructose), a disaccharide (e.g., maltose and sucrose), an oligosaccharide, a polysaccharide (e.g., dextrin and cyclodextrin), or a sugar alcohol (e.g., xylitol, sorbitol, and erythritol). Natural flavoring agents (e.g., thaumatin and stevia extracts) and synthetic flavoring agents (e.g., saccharin and aspartame) may be used as the flavoring agent. It may further contain various nutrients, a vitamin, an electrolyte, a flavoring agent, a colorant, pectic acid or a salt thereof, alginic acid or a salt thereof, an organic acid, a protective colloidal thickening agent, a pH controlling agent, a stabilizer, a preservative, glycerin, alcohol, a carbonating agent as used in carbonated beverages, etc. in addition to the healthy functional food composition.

The present invention also relates to a pharmaceutical composition containing *Dolichos lablab* Linn. extract as an active ingredient for easing hangovers, and preventing or treating alcoholic gastrointestinal diseases The pharmaceutical compositions of the present invention may further contain a suitable carrier, excipient or diluent conventionally used in the preparation thereof. The pharmaceutical dosage form of the composition according to the present invention may be used alone or as a combination or an appropriate assembly with other pharmaceutically active compounds. The pharmaceutical composition according to the present invention may be formulated into oral formulations such as powders, granules, tablets, capsules, suspensions, emulsions, syrups, and aerosols, external applications, suppositories, and injections according to the respective conventional method. Examples of the carrier, excipient and diluent that can be included in the pharmaceutical composition containing the extract include a variety of compounds or mixtures, such as lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil. When the composition is formulated, generally used diluents or excipients such as fillers, extenders, binders, humectants, disintegrants, and surfactants are used. Examples of solid preparations for oral administration include tablets, pills, powders, granules, and capsules, and are prepared by mixing the mixed extract with at least one excipient, for example, starch, calcium carbonate, sucrose or lactose, and gelatin. Further, lubricants such as magnesium stearate and talc are also used in addition to simple excipients. Examples of liquid preparations for oral administration include suspensions, liquids for internal use, emulsions, and syrups, and they may contain various excipients such as humectants, sweeteners, flavoring agents, preservatives, as well as water and liquid paraffin, which are generally used simple diluents. Examples of formulations for parenteral administration include sterile aqueous solutions, non-aqueous solvents, suspensions, emulsions, lyophilized formulations, and suppositories. Examples of the non-aqueous solvents and the suspension solvents include propylene glycol, polyethylene glycol, vegetable oil such as olive oil, and injectable esters such as ethyl oleate. Examples of the matrix for suppositories include witepsol, macrogol, tween 61, cacao butter, laurinum, and glycerogelatin. The preferred dosage of the therapeutic composition of the present invention varies depending on the condition and weight of the patient, the severity of the disease, the form of the drug, and the administration route and period. However, it can be suitably selected by those skilled in the art. The pharmaceutical composition of the present invention may be administered to mammals such as rats, mice, livestock and humans through various routes. All of the administration methods are predictable. For example, it may be administered orally, rectally or intravenously, or through an intramuscular, subcutaneous, intrauterine dura mater or intracerebroventricular injection.

EXAMPLES

Hereinafter, the present invention will be described in more detail with reference to examples. It will be apparent to those skilled in the art that these examples are for illustrative purposes only, and the scope of the present invention is not limited by these examples.

Example 1

Preparation of *Dolichos lablab* Linn. Extract (1) Preparation of a Hot Water Extract of *Dolichos lablab* Linn.

2 L of water was added to 200 g of *Dolichos lablab* Linn., followed by heating at 90 to 100° C. for 2 to 3 hours. The extract was then filtered and then dried under reduced pressure using a lyophilizer to obtain a hot water extract of *Dolichos lablab* Linn. The extract was dissolved in sterilized water for use in experiments.

(2) Preparation of an Ethanol Extract of *Dolichos lablab* Linn.

2 L of 80% ethanol was added to 200 g of *Dolichos lablab* Linn., followed by immersion at a room temperature of 20 to 25 for 22° C. to 24 hours. The extract was then filtered, concentrated with a vacuum concentrator, and then dried under reduced pressure using a lyophilizer to obtain an ethanol extract of *Dolichos lablab* Linn. The extract was dissolved in sterilized water for use in experiments.

Example 2

Evaluation of the Effect of a Hot Water Extract of *Dolichos lablab* Linn. in Reducing Ethanol in the Blood In Example 2, the effect of the hot water extract of *Dolichos lablab* Linn. of the present invention on the blood ethanol concentration increased by ethanol consumption was determined.

6-week-old (n=5) male SD rats were divided into three groups. The first group was a control group not subjected to any treatment, and the second group was an ethanol-administered group (alcohol+vehicle) which was administered with 20% (v/v) ethanol for 2 days and with 40% (v/v) ethanol on the third day. The third group was a *Dolichos lablab* Linn. extract-administered group which was pretreated with 400 mg/kg of *Dolichos lablab* Linn. extract for 3 days prior to administration of ethanol, and then administered with 400 mg/kg of *Dolichos lablab* Linn. extract 30 minutes prior to administration of ethanol. The blood collected from the orbital and the blood collected from the abdominal vena cava 30 minutes, 60 minutes, 120 minutes and 180 minutes after the last administration of ethanol and the *Dolichos lablab* Linn. extract was centrifuged at 3000 rpm for 20 minutes. The concentration of ethanol contained in the thus-obtained serum was measured with an ethanol measuring kit (Abcam, ab65343).

Figure 1:
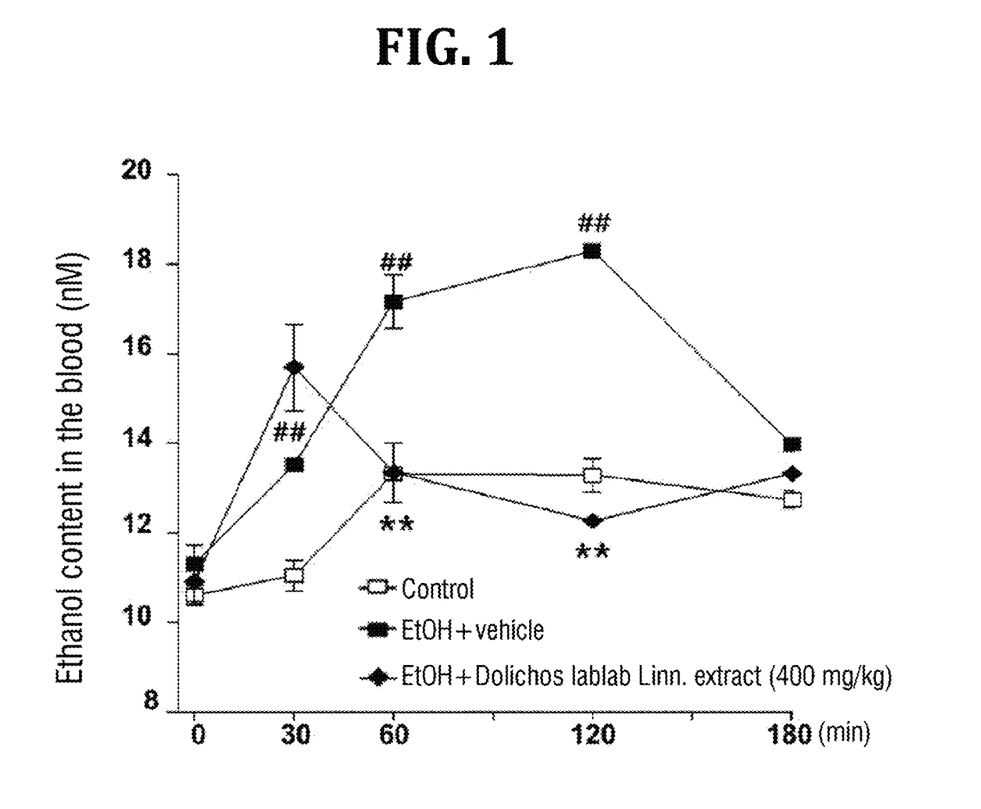
FIG. 1 shows the results of measurement of the ethanol content in the blood over time (0, 30, 60, 120 and 180 minutes) after administration of ethanol and administration of the *Dolichos lablab* Linn. extract of the present invention. "Control" represents a normal group not subjected to any treatment. "EtOH+vehicle" represents a group administered with ethanol. "EtOH+*Dolichos lablab* Linn. extract (400 mg/kg)" represents a group administered with ethanol and *Dolichos lablab* Linn. extract. "##" indicates that the blood ethanol content of the ethanol-administered group statistically significantly increased with $p<0.01$ compared to the normal group. "**" indicates that the blood ethanol content of the group administered with ethanol and *Dolichos lablab* Linn. extract statistically significantly decreased with $p<0.01$ compared to the ethanol-administered group.

As a result, as shown in FIG. 1, it was found that the blood ethanol concentration resulting from ethanol consumption significantly increased until 2 hours, and then returned to almost normal level at 3 hours. Meanwhile, in the *Dolichos*

*lablab* Linn. extract-administered group, ethanol in the blood were rapidly degraded compared with the ethanol-administered group, so that the blood ethanol concentration statistically significantly decreased from 1 hour and was maintained until 2 hours.

Example 3

Evaluation of the Aldehyde Dehydrogenase (ALDH) Activity and Acetaldehyde (ADH) Production in the Blood of a Hot Water Extract of *Dolichos lablab* Linn The ALDH activity and ADH content were measured using the serum obtained in Example 2 above. The ALDH activity was measured using an aldehyde dehydrogenase activity colorimetric assay kit (BioVision), and ADH was measured using an aldehyde quantification assay kit.

Figure 2A:
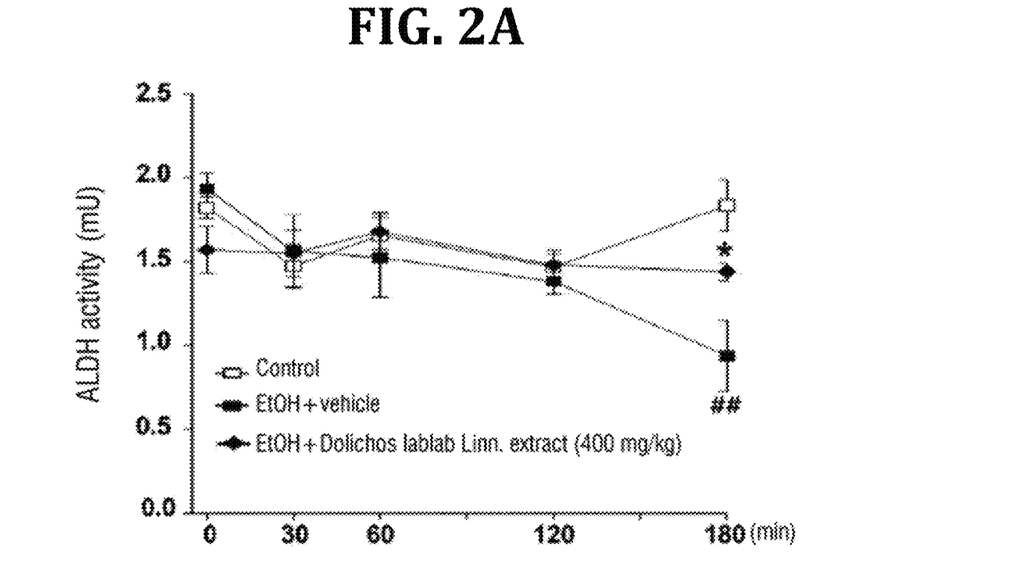
FIG. 2A shows aldehyde dehydrogenase (ALDH) activity.

As a result, as shown in FIG. 2A, it was found that the aldehyde dehydrogenase activity tended to gradually decrease with the administration of ethanol, but that the aldehyde dehydrogenase activity was maintained in the group administered with the hot water extract of *Dolichos lablab* Linn of the present invention.

Figure 2B:
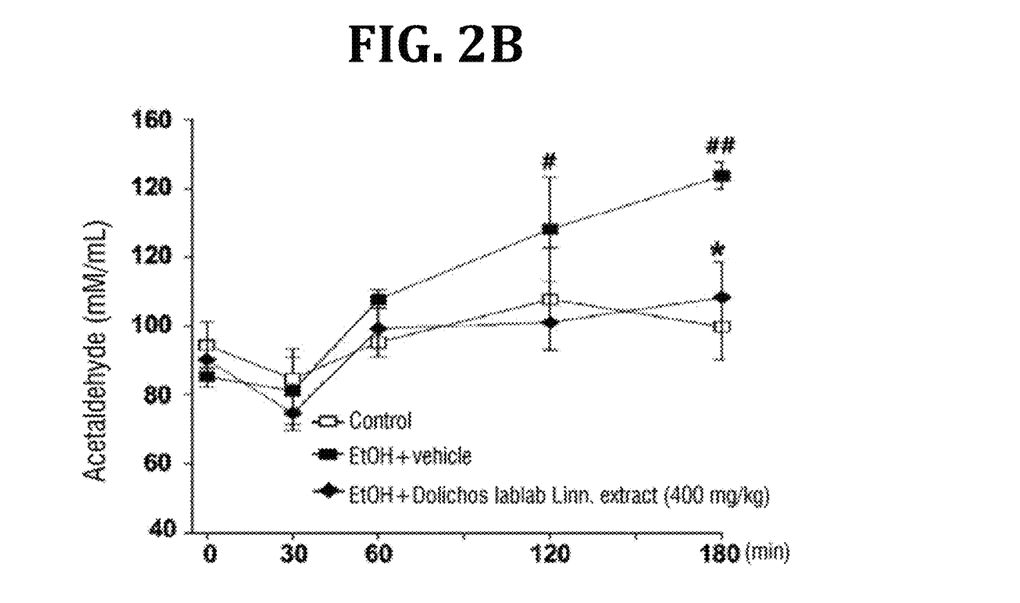

The blood acetaldehyde concentration of the ethanol-administered group continuously increased for 3 hours. However, the concentration in the group administered with the hot water extract of *Dolichos lablab* Linn of the present invention was maintained at a level almost similar to that of the normal group (FIG. 2B).

Example 4

Evaluation of the Effect of a Hot Water Extract of *Dolichos Lablab* Linn. on the Stomach and Liver Damage Caused by Alcohol After the blood was collected in Example 2, the animal models were sacrificed and the stomach and liver tissues were stained with H&E to determine whether there was gastrointestinal and liver damage caused by ethanol consumption, and whether the hot water extract of *Dolichos lablab* Linn. of the present invention alleviated gastrointestinal and liver damage.

Figure 3A:
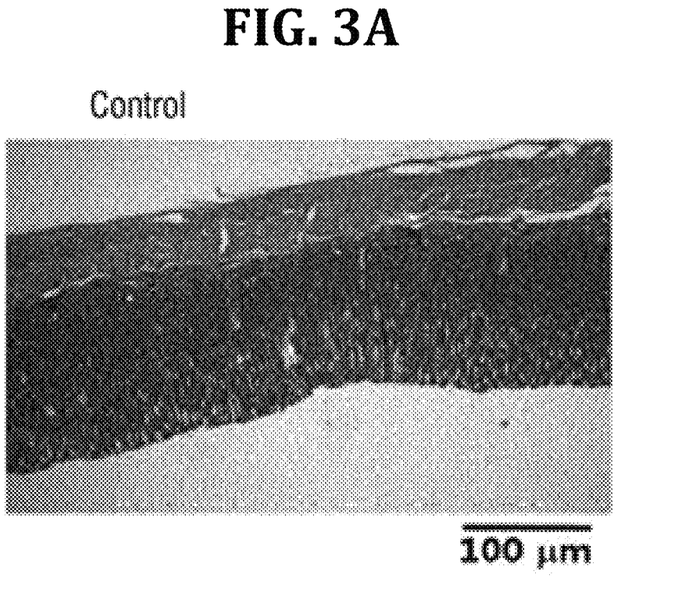
FIG. 3A shows normal stomach tissues.
Figure 3B:
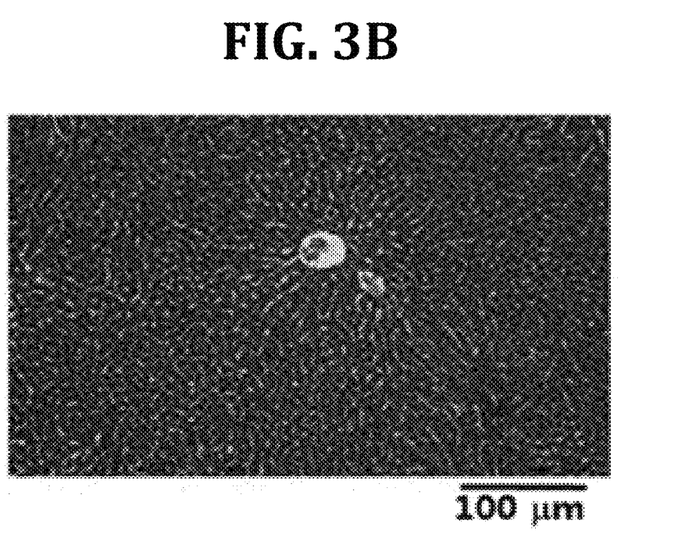
FIG. 3B shows normal liver tissues.
Figure 3C:
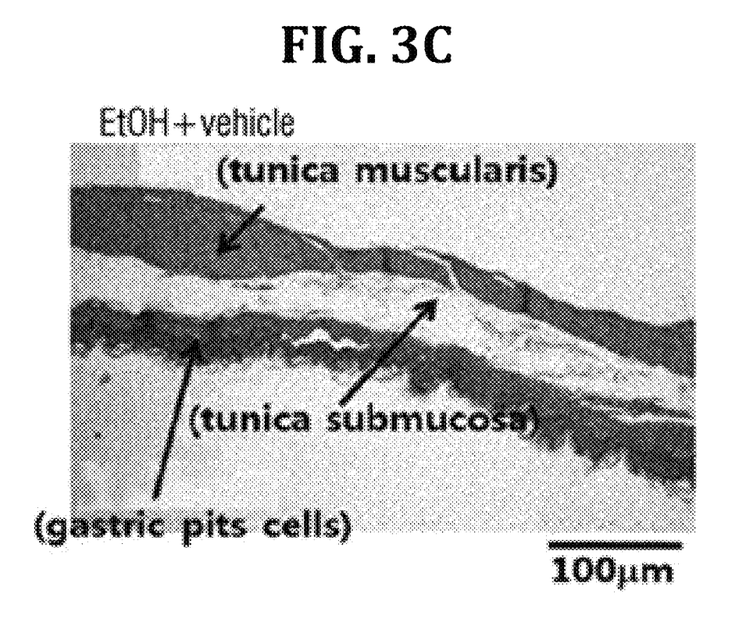
FIG. 3C shows the stomach tissues of the ethanol-administered group.
Figure 3D:
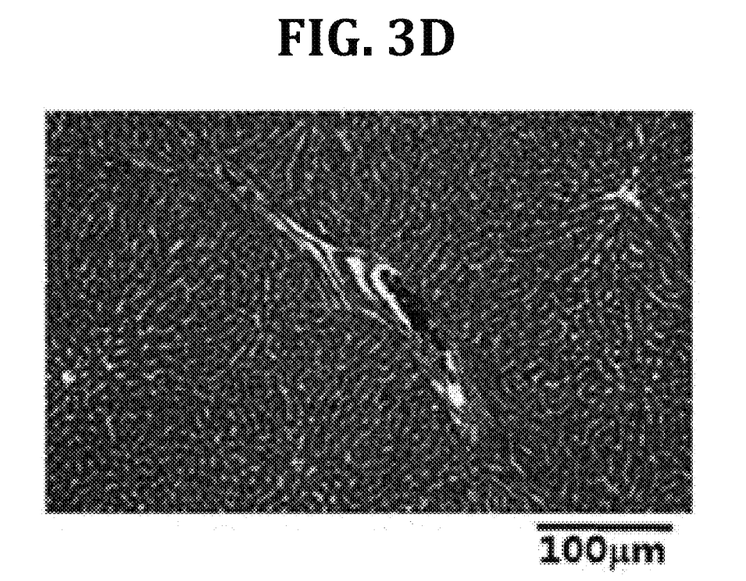
FIG. 3D shows the liver tissues of the ethanol-administered group.
Figure 3E:
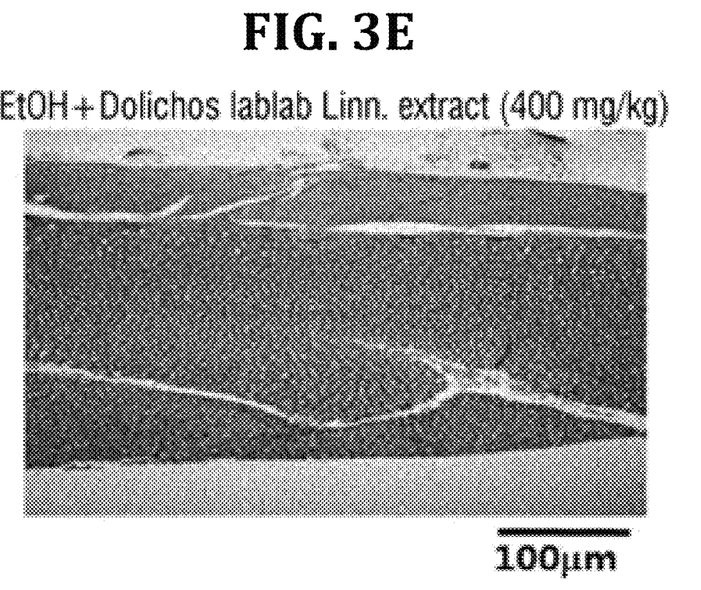
FIG. 3E shows the stomach tissues administered with ethanol and *Dolichos lablab* Linn. extract.

As a result, as can be seen in the staining pictures of the gastrointestinal tissues in FIGS. 3A to 3F, the following was observed in the ethanol-administered group: The tunica muscularis region, which is the outermost part of the gastrointestinal tissues, was damaged, and the tunica submucosa, which is located below the mucosa of the gastrointestinal tissues and rich in collagen and allows the stomach to efficiently expand when the food enters, was damaged, resulting in a large gap between the tunica submucosa and the basement membrane. Epithelium stem cells grow in the basement membrane region. However, damage to the epithelium region of the stomach was also observed. Also, the gastric pits cells at the outermost side were severely damaged (FIG. 3C). The role of gastric pits cells is to sense substances to be digested and cause stimulation to secrete digestive enzymes. In contrast, in the group administered with the *Dolichos lablab* Linn. extract of the present invention, the pathological conditions induced by ethanol were significantly alleviated and there was little difference from the normal group (FIG. 3E).

Figure 4A:
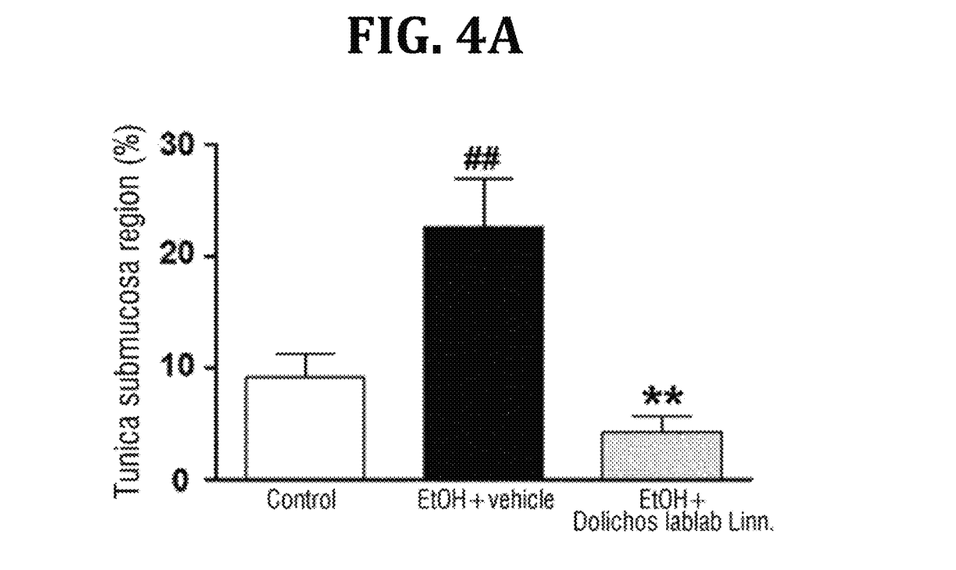
FIGS. 4A and 4B show the areas of the stomach tissues (normal tissues) not administered with ethanol, the stomach tissues of the ethanol-administered group, and the gastric pits cells and the tunica submucosa of the group administered with ethanol and *Dolichos lablab* Linn. extract in the results of H&E staining of stomach and liver tissues to determine the effect of a hot water extract of *Dolichos lablab* Linn. on the stomach and liver damage caused by alcohol. "Control" represents a normal group not subjected to any treatment. "EtOH+vehicle" represents a group administered with ethanol. "EtOH+*Dolichos lablab* Linn. extract (400 mg/kg)" represents a group administered with ethanol and *Dolichos lablab* Linn. extract. "##" indicates that the area of the ethanol-administered group (EtOH+vehicle) is statistically significantly different from that of the control group with $p<0.01$. "**" indicates that the area of the group administered with ethanol and *Dolichos lablab* Linn. extract (EtOH+*Dolichos lablab* Linn.) is statistically significantly different from that of the ethanol-administered group with $p<0.01$.
Figure 4B:
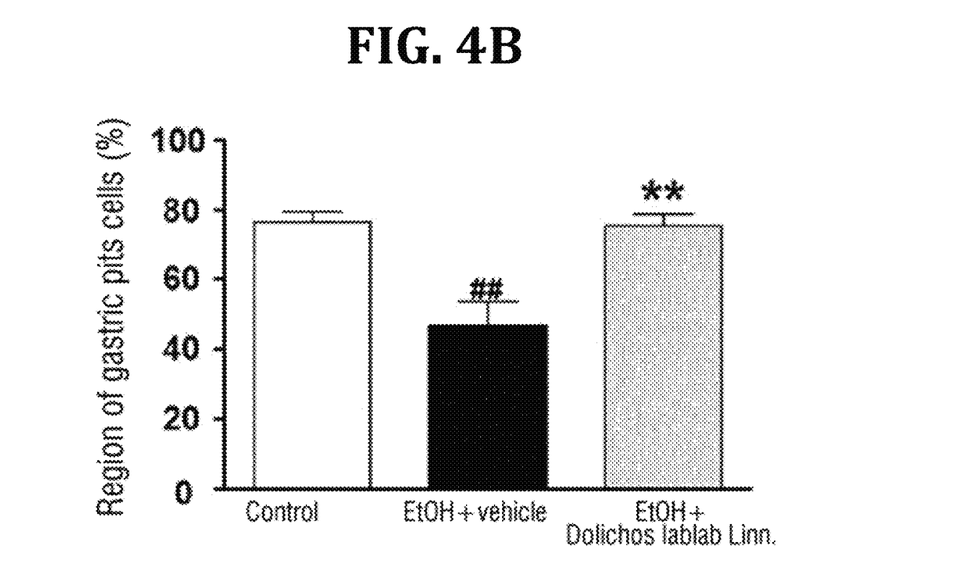

As shown in FIGS. 4A and 4B, the areas of the gastric pits cells and tunica submucosa were quantified from the H&E results of the gastrointestinal tissues using the Image J program. As a result, it was found that the administration of ethanol decreased the area of the gastric pits tissues statistically significantly compared to the group not administered with ethanol, but that the group administered with both ethanol and *Dolichos lablab* Linn. extract did not show a decrease in the area of the gastric pits tissues and had an almost similar area to the normal level. In the case of the tunica submucosa, the area thereof was significantly increased by the administration of ethanol, but the area of the group administered with both ethanol and *Dolichos lablab* Linn. extract was almost similar to that of the group not subjected to any treatment.

Figure 3F:
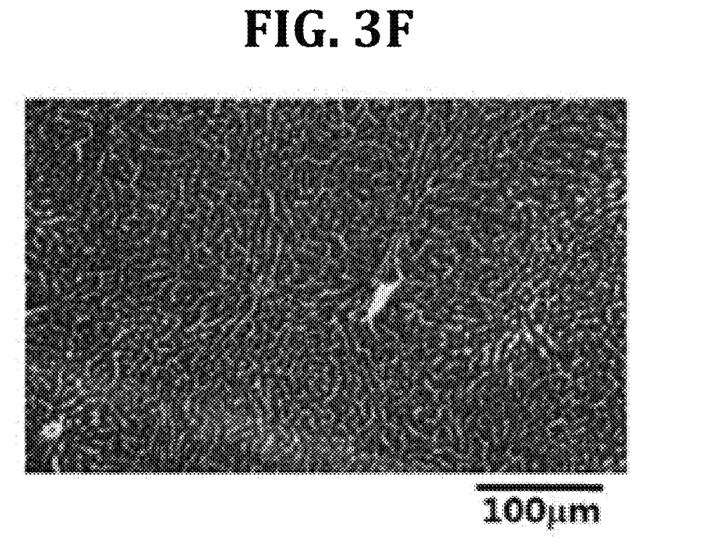
FIG. 3F shows the liver tissues administered with ethanol and *Dolichos lablab* Linn. extract. "Control" represents a normal group not subjected to any treatment. "EtOH+vehicle" represents a group administered with ethanol. "EtOH+*Dolichos lablab* Linn. extract (400 mg/kg)" represents a group administered with ethanol and *Dolichos lablab* Linn. extract.

Meanwhile, the effect of *Dolichos lablab* Linn extract could not be determined from the liver tissue staining results as shown in FIG. 3B, FIG. 3D and FIG. 3F because the liver tissues were not damaged by short-term (3 days) ethanol administration.

The invention claimed is:

1. A method for alleviating alcoholic gastrointestinal diseases, comprising:
    administering a composition consisting of a pharmaceutically effective amount of *Dolichos lablab* Linn. extract as an active ingredient to a subject having alcoholic gastrointestinal diseases,
    wherein the alcoholic gastrointestinal diseases are alcoholic gastritis or alcoholic gastric ulcer;
    wherein the *Dolichos lablab* Linn. extract promotes the degradation of alcohol and acetaldehyde in the blood and increases aldehyde dehydrogenase activity; and
    wherein the *Dolichos lablab* Linn. extract is extracted using hot water by a method comprising:
    adding water in an amount of 0.5 to 1 liter per 100 grams of *Dolichos lablab* Linn.;
    heating to 90 to 110° C. for 2 to 3 hours to form the extract;
    separating the extract from the *Dolichos lablab* Linn.; and removing the water from the extract.

2. The method for alleviating alcoholic gastrointestinal diseases according to claim 1, wherein the composition is prepared into a formulation selected from powders, granules, pills, tablets, capsules, candies, syrups and beverages.

3. The method for alleviating alcoholic gastrointestinal diseases according to claim 1, wherein the composition further comprises a pharmaceutically acceptable carrier, excipient or diluent in addition to the active ingredient.

4. The method for alleviating alcoholic gastrointestinal diseases according to claim 1, wherein the pharmaceutically effective amount of *Dolichos lablab* Linn. extract is 400 mg/kg.

5. A method for treating alcoholic gastrointestinal diseases, comprising:
    administering a composition consisting of a pharmaceutically effective amount of *Dolichos lablab* Linn. extract as an active ingredient to a subject having alcoholic gastrointestinal diseases,
    wherein the alcoholic gastrointestinal diseases are alcoholic gastritis or alcoholic gastric ulcer; and
    wherein the *Dolichos lablab* Linn. extract promotes the degradation of alcohol and acetaldehyde in the blood and increases aldehyde dehydrogenase activity; and
    wherein the *Dolichos lablab* Linn. extract is extracted using hot water by a method comprising:
    adding water in an amount of 0.5 to 1 liter per 100 grams of *Dolichos lablab* Linn.;
    heating to 90 to 110° C. for 2 to 3 hours to form the extract;
    separating the extract from the *Dolichos lablab* Linn; and removing the water from the extract.

6. The method for treating alcoholic gastrointestinal diseases according to claim 5, wherein the composition further comprises a pharmaceutically acceptable carrier, excipient or diluent in addition to the active ingredient.

7. The method for treating alcoholic gastrointestinal diseases according to claim 5, wherein the composition is prepared into a formulation selected from capsules, powders, granules, tablets, suspensions, emulsions, syrups, and aerosols.

8. The method for treating alcoholic gastrointestinal diseases according to claim 5, wherein the pharmaceutically effective amount of *Dolichos lablab* Linn. extract is 400 mg/kg.

* * * * *